United States Patent
Kiuchi et al.

(10) Patent No.: US 6,287,010 B1
(45) Date of Patent: Sep. 11, 2001

(54) ROLLING BEARING

(75) Inventors: Akihiro Kiuchi; Manabu Ohori, both of Kanagawa (JP)

(73) Assignee: NSK Ltd., Tokyo (JP)

( * ) Notice: Subject to any disclaimer, the term of this patent is extended or adjusted under 35 U.S.C. 154(b) by 0 days.

(21) Appl. No.: 09/428,792

(22) Filed: Oct. 28, 1999

(30) Foreign Application Priority Data

Oct. 28, 1998 (JP) .................................................. 10-307427

(51) Int. Cl.$^7$ ...................................................... F16C 33/58
(52) U.S. Cl. ............................................. 384/492; 384/912
(58) Field of Search ................................... 384/492, 569, 384/912, 913

(56) References Cited

U.S. PATENT DOCUMENTS

| | | | |
|---|---|---|---|
| 5,005,417 | 4/1991 | Kawasaki et al. | 73/593 |
| 5,147,140 | * 9/1992 | Murakami et al. | 384/492 |
| 5,259,886 | * 11/1993 | Utsumi et al. | 384/912 X |
| 5,527,401 | * 6/1996 | Kim | 148/648 |
| 5,788,923 | * 8/1998 | Hayashi et al. | 420/104 |
| 6,066,068 | * 5/2000 | Takemura et al. | 384/912 X |
| 6,165,289 | * 12/2000 | Matsumoto et al. | 384/492 X |

FOREIGN PATENT DOCUMENTS

| | | | |
|---|---|---|---|
| 468 009 | 3/1969 | (CS) | G01N/29/00 |
| 38 10906 A1 | 11/1988 | (DE) | G01N/29/04 |
| 39 22 720 C2 | 10/1991 | (DE) | C21D/9/40 |
| 690 27 898 T2 | 1/1997 | (DE) | G01N/29/00 |
| 197 14 948 A1 | 11/1997 | (DE) | F16C/33/62 |
| 197 33 101 C2 | 3/1999 | (DE) | F16C/33/62 |
| 3-56640 | 3/1991 | (JP) . | |
| 5-117804 | 5/1993 | (JP) . | |
| 6-145883 | 5/1994 | (JP) . | |
| 6-192790 | 7/1994 | (JP) . | |
| 7-109541 | 4/1995 | (JP) . | |

* cited by examiner

*Primary Examiner*—Thomas R. Hannon
(74) *Attorney, Agent, or Firm*—Sughrue, Mion, Zinn, Macpeak & Seas, PLLC

(57) ABSTRACT

In view of the fact that, when backup roll bearings which have been found satisfactory in the purity thereof in the sample evaluation through observations using a microscope are checked many times for the top surface layer portions of the raceway surfaces thereof according to an ultrasonic detecting method, on quite rare occasions, there can be found a bearing which contains one or more inclusions each having a size of as large as several hundreds $\mu$m, and such inclusions give rise to occurrence of a short-life bearing as a finished product, a range expressed by 2% Da depth× raceway surface is used as a test piece volume and the size of a non-metallic inclusion existing in the test piece volume is restricted to a length less than 500 $\mu$m, preferably, less than 100 $\mu$m. Here, the term "2% Da depth" means a depth up to 2% of a rolling element mean diameter from the surface of an inner or outer race of a bearing.

4 Claims, 2 Drawing Sheets

ROLLING BEARING

BACKGROUND OF THE INVENTION

1. Field of the Invention

The present invention relates to a rolling bearing and, in particular, to a rolling bearing such as a bearing for iron and steel represented by a roll neck bearing which, even under a severe using condition of a high load and a high surface pressure, does not produce an unexpected short life product but can be guaranteed to have a stable life.

2. Related Art

Recently, a bearing using environment has been severer and severer and, in a bearing to be used in iron and steel facilities, a load and a surface pressure to be applied to the bearing have been higher and higher. In such severe condition, as the bearing to be used in iron and steel facilities, there is more and more strongly required a bearing which not only can provide a long life but also can stamp out a short-life bearing occurring unexpectedly. The reason for this requirement is as follows: that is, in a continuous production system in which the inspection and maintenance of a production line are carried out every preset given time, if there occurs a short-life bearing which comes short of the given operating time, then the production line is caused to stop within the operating time, which incurs great damage.

As one of factors that block the durability of the bearing, there is found a defect or damage in the material of the bearing. For steel material used to produce a bearing, recently, there has been employed a method in which, after the steel material is rolled into a steel bar, for example, in a steel making process, all steel bars are checked for internal defects thereof using ultrasonic waves or the like (see Special Steel, vol. 46, No. 6, page 31, edited by Special Steel Club Co.). The main object of this inter-process defect checking method is to detect a hole (a defect) existing in the inside of the steel material, such as a macro-streak-flaw, a blow hole, or an unpressed portion left in a rolling and forging operation, or the like; and, this method uses a low frequency in the range of 2–5 MHz for detection of the hole or defect. Thanks to this method, there has been eliminated a large-sized defect of the order of several mm. However, in the steel material that has been rolled but left as it is, the crystal grain of the inside thereof and the surface layer thereof are rough, thereby causing the noise to become large, which in turn makes it impossible to detect the defect with high accuracy.

On the other hand, it is known that a non-metallic inclusion (intervening material) existing in the material of a bearing has a great influence on the life of the bearing itself. For example, in steel making facilities, a backup roll bearing is used under a high load and in a well-lubricated condition given mainly by oil lubrication; and, when the bearing is used in such lubrication condition, it has been recently found that, if any non-metallic inclusion exists in the vicinity of the surface layer portion of the raceway surface of an inner or outer race of the bearing, then such non-metallic inclusion causes a defect such as a crack or the like in the bearing, thereby reducing the life of the bearing.

In order to avoid the above problem, recently, there have been proposed many proposals each of which specifies the number of hard inclusions (mainly, inclusions belonging to oxide-system materials consisting mainly of $Al^2 O^3$, or inclusions belonging to Ti-system materials consisting mainly of TiN) to thereby enhance the purity of the bearing greatly and thus extend the life of the bearing.

For example, according to Japanese Patent Publication No. 6-145883 of Heisei, there is disclosed a method in which highly-purified steel including within nine pieces of $Al^2 O^3$ of 10 $\mu$m or more existing and within nine pieces of TiN of 5 m in an area to be checked of 320 $mm^2$ is used to thereby be able to guarantee the long life of the bearing. As similar examples aiming at extending the life of the bearing by limiting the number of the non-metallic inclusions, there are also known Japanese Patent Publication No. 3-56640 of Heisei and Japanese Patent Publication No. 7-109541 of Heisei respectively filed by the present applicants, as well as Japanese Patent Publication No. 5-117804 of Heisei, Japanese Patent Publication No. 6-192790 of Heisei, and the like.

Every one of the technologies disclosed in the above-cited publications, when specifying the quantity of inclusions, observes a very tiny given area of, for example, 320 $mm^2$ or 165 $mm^2$ by a microscope or the like and specifies the purity of the steel material in accordance with the number of inclusions detected in such given area.

However, although the purity of the steel material is enhanced in the above-mentioned manner, all the products made of the steel material are not inspected and verified for the number of inclusions. In other words, every one of the above technologies, simply by observing the very tiny given area of the bearing material representatively, evaluates the purity of the whole bearing and the bearing material.

The present inventors have taken up this problem and made every effort to solve this problem. For example, when many raceway surface layer portions of inner and outer races of bearings for backup rolls used in a rolling mill were checked by an ultrasonic detecting method, it has been found that, even in bearings the purity of which was found satisfactory in a sample evaluation through observations using a microscope, on quite rare occasions, there can be found a bearing in which an inclusion of as large as several hundreds $\mu$m exists in the range from the raceway surface of the inner or outer race of the bearing up to the depth of several mm or so.

That is, even if a good result is obtained by checking the tiny range of an area to be checked in the top surface of the raceway surface of the inner or outer race of the bearing, it cannot be always guaranteed that an inclusion of a large size is absent in the bearing. Much less, in the case of a large-sized bearing such as a backup roll bearing or the like, a relatively large load is applied to the bearing because the area of the raceway surface thereof is large, and the depth of the portion thereof to which a stress is applied is thereby caused to increase. Therefore, simply by accurately inspecting only the raceway surface of the bearing as in the conventional method, it is difficult to eradicate a short-life bearing which can occur unexpectedly.

SUMMARY OF THE INVENTION

The present invention has been made by directing our attention to the fact that, when a bearing is formed of a steel material, the existing position of a non-metallic inclusion in the bearing constitutes an important factor for the long life of the bearing. Accordingly, it is an object of the invention to provide a rolling bearing which is guaranteed free from an internal defect in the range from the rolling contact surface thereof, where its inner or outer race and rolling elements are rollingly contacted with each other, to a given depth and thus, even when it is used under a severe environment of a high load and a high surface pressure as in a bearing for iron and steel, can avoid a fear of occurrence of a short-life bearing as a finished product to thereby provide a long-life rolling bearing.

In attaining the above object, according to an aspect of the present invention, there is provided a rolling bearing including at least of an inner race, an outer race, and a plurality of rolling elements rollingly movable on the inner or outer race, wherein a non-metallic inclusion existing in a test piece, which has a length of less than 500 μm within 2% Da×raceway surface of said inner or outer race.

Here, the term "2% Da depth" expresses a depth which ranges from the surfaces of the inner and outer races and rolling elements of the bearing to 2% of the mean diameter of the rolling elements.

In a rolling bearing according to the invention, at least as material for the inner and outer races thereof, there can be used steel material which contains, as impurity components, oxygen (O) of 9 ppm or less and sulfur (S) of 0.005% by weight.

DETAILED DESCRIPTION OF PREFERRED EMBODIMENTS

Figure 1:
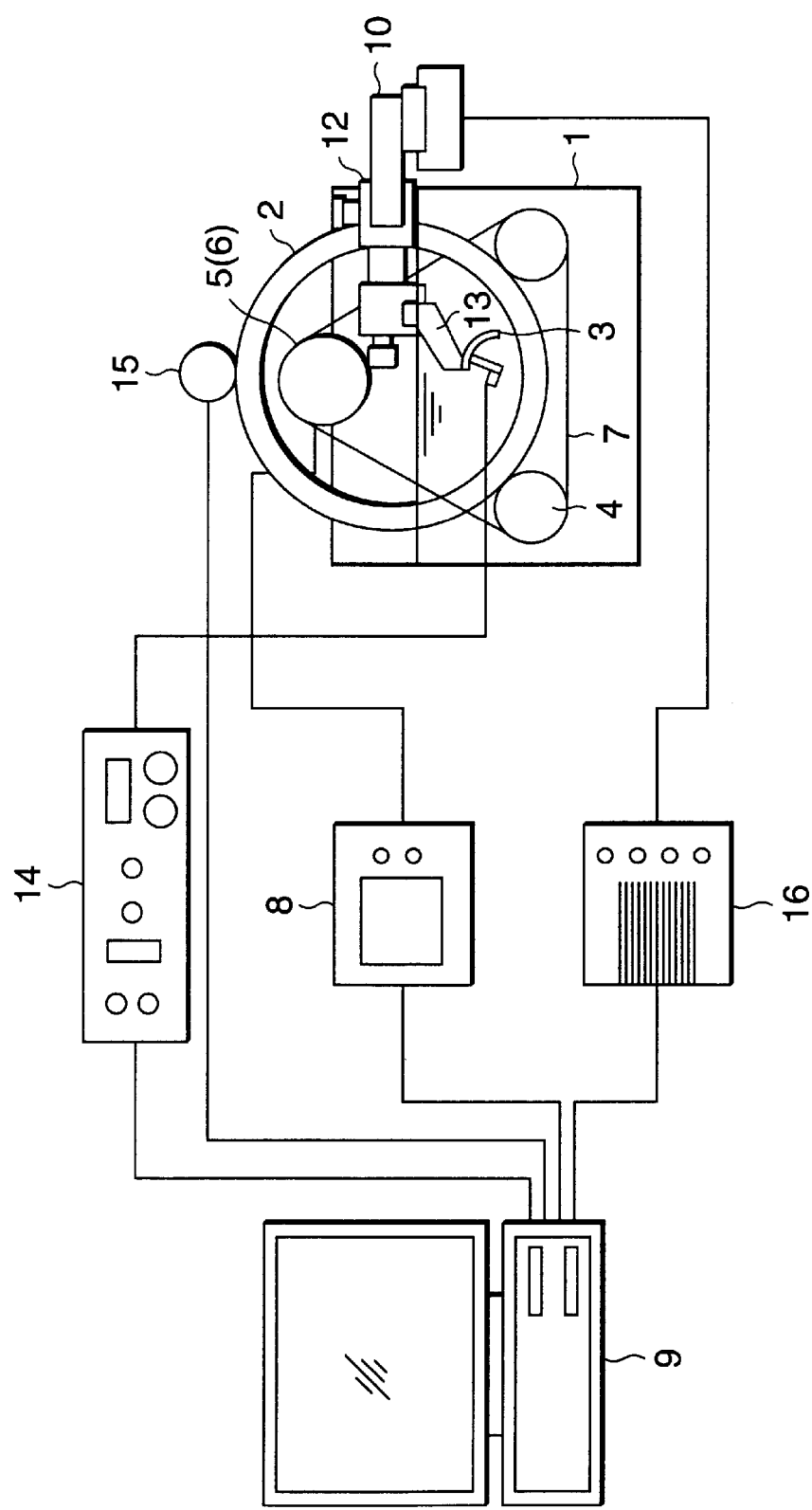
FIG. 1 is a schematic view of an example of an ultrasonic detective device which can be used in the invention; and, FIG. 2 is a section view of the main portions of a life tester which is used to test the life of a bearing.

Now, description will be given below of the preferred embodiments of a rolling bearing according to the invention with reference to the accompanying drawings.

First Embodiment

When the present inventors have examined in detail a large defective echo portion which can be detected very rarely in the above-mentioned ultrasonic detecting method for detecting a defect in the raceway surface of a bearing such as a backup roll bearing, it has been found that a large non-metallic inclusion of as large as several hundreds μm can exist in the defective echo portion.

Therefore, a large number of tests have been carried out on the life of the present bearing to find out the correlation between the strength of the defective echo portion, the length and size of an inclusion detected, and the life of the bearing. As a result, if a non-metallic inclusion having a length of 500 μm or more exists within the 2% Da depth range, then it has been found that the life of the bearing is shortened extremely. Especially, if a non-metallic inclusion having a length of 100 μm or more does not exist within the above-mentioned depth range, then it has been found that a further stable life can be obtained.

In the present invention, the reason why the existing position of the large inclusion is specified within 2% Da range is that a depth, where a shearing stress generated when the outer and inner races and rolling elements of the rolling bearing are rollingly contacted with each other provides the largest value, is less than 2% of the mean diameter of the rolling element from the surface of the rolling contact surface thereof, and also that the present shearing stress acts on the large non-metallic inclusion to thereby cause the bearing to break away.

Now, illustrations will be given below of the volumes of the test pieces of the present invention and the prior art.

1) In the case of 850RV1133 (a quadruple row cylindrical roller bearing)

When there is used a roller bearing having the following dimensions, that is, the inner race inside diameter; 850 mm: the outer race outside diameter 1180 mm, the width 650 mm, and roller diameter 80 mm, if the volumes of the test pieces of the outer and inner races of the bearing up to the 2%Da depth thereof are calculated, then the inner race provides a volume of approx. $3.1 \times 10^6$ mm$^3$ and the outer race provides a volume of approx. $3.0 \times 10^6$ mm$^3$.

Thus, as the sum of the inner and outer races of the present roller bearing, there is obtained a volume of $6.1 \times 10^6$ mm$^3$ in all.

2) In the case of NU3336 (a cylindrical roller bearing)

When there is used a roller bearing having the following dimensions, that is, the inner race inside diameter; 180 mm: the outer race outside diameter 380 mm, the width 150 mm, and roller diameter 48 mm, if the volumes of the test pieces of the outer and inner races of the bearing up to the 2%Da depth thereof are calculated, then the inner race provides a volume of approx. $1.1 \times 10^5$ mm$^3$ and the outer race provides a volume of approx. $1.5 \times 10^5$ mm$^3$. Thus, similarly, as the sum of the inner and outer races of the present roller bearing, there is obtained a volume of $2.6 \times 10^5$ mm$^3$ in all.

On the other hand, if a single roller bearing according to the above-mentioned prior art is sliced in the form of a cube having an area of 320 mm$^2$ and a depth of 10 μm and the volume of the present cubic slice is calculated, then there is obtained a volume of approx. 3.2 mm$^3$ which corresponds to one of two test pieces of a single roller bearing according to the prior art. Thus, similarly to the above, if this volume is doubled to find the volume of the two test pieces of the single roller bearing according to the prior art, then there is obtained a volume 6.2 mm$^3$.

As can be clearly understood from the above examples, the test piece volume for inspecting a non-metallic inclusion according to the invention is larger by far than the prior art and, therefore, the correlation between the test piece volume and bearing life is similarly very higher in reliability, and the non-metallic inclusion inspection or detection according to the invention can be carried out in a non-destructive manner.

In the present invention, to detect the presence or absence of a non-metallic inclusion within the test piece volume of 2% Da×raceway surface, preferably, the non-metallic inclusion may be ultrasonically detected using a detection probe of 2–30 MHz according to a surface wave detecting method or an angle incidence detecting method. If the frequency of the detection probe is less than 2 MHz, then there is a possibility that a non-metallic inclusion having a length of 100 μm cannot be detected.

On the other hand, if the frequency of the detection probe exceeds 30 MHz, then the ultrasonic wave attenuates greatly within the bearing to thereby be unable to detect up to the 2% Da depth. By the way, it is said that the defect detecting limit in the ultrasonic detecting method is ½ of the wavelength; and, when detecting a non-metallic inclusion of 100 μm or more according to an angle beam detecting method using a transversal wave (the sound speed of a transversal wave through steel is 3230 m/s), a frequency used is 16 MHz or higher.

Now, description will be given below of a comparison test which was conducted on embodiments according to the invention and comparison examples.

In the comparison test, as test pieces, there were prepared cylindrical roller bearings of a type NU3336 respectively formed of materials shown in Table 1, and the raceway surfaces of the inner and outer races of these bearings were inspected for defects by an ultrasonic detecting device.

TABLE 1

| Division | No. | Steel Kinds | Non-metallic inclusion 500 μm or more | Non-metallic inclusion 100 μm or more | Bearing Life Test |
|---|---|---|---|---|---|
| Embodiment 1 | 1 | SUJ2 | No | No | 100 Hrs. or longer |
| Embodiment 2 | 2 | SCR420 | No | No | 100 Hrs. or longer |
| Comparison example 1 | 3 | SCR420 | Present (two) | Present (five) | 12 Hrs. |
| Comparison example 1 | 4 | SUJ2 | Present (one) | Present (four) | 15 Hrs. |
| Comparison example 1 | 5 | SCR440 | No | Present (two) | 60 Hrs. |

Now, FIG. 1 is a schematic view of the ultrasonic detecting device used in the comparison test. In FIG. 1, reference character 1 designates a water tank in which there is stored water used as an ultrasonic wave transmission medium. Within the water tank 1, there are disposed a bearing ring 2, which is a finished product of an outer race (or an inner race) of a rolling bearing to be tested, and an ultrasonic detecting probe 3 in such a manner that they are respectively immersed in the water. As the ultrasonic detecting probe 3, there is used a focusing type probe which is strong in directivity and hard to be influenced by the curvature of the bearing ring 2.

The bearing ring 2 is carried on two pulleys 4 disposed within the water tank 1 and spaced apart from each other in the horizontal direction, and a belt 7 is wound in an equilateral-triangle manner around the two pulleys 4 and another pulley 6 fixed to the motor shaft of a rotation drive motor 5.

The rotation drive motor 5 can be controlled through a motor driving control amplifier 8 by a control unit 9 and, if the rotation drive motor 5 is driven, then the bearing ring 2 carried on the two pulleys 4 can be rotated at a given speed. By the way, the control unit 9 is composed of a personal computer including display means such as a CRT and the like.

The ultrasonic detecting probe 3 is mounted through a probe mounting member 13 on an XY stage 12 supported by a linear guide device 10 which is disposed in such a manner that it can be moved along the axial direction of the bearing ring 2, and the ultrasonic detecting probe 3 is so disposed as to be opposed to the raceway surface of the bearing ring 2. Also, the ultrasonic detecting probe 3 not only transmits an ultrasonic pulse corresponding to a voltage signal from an ultrasonic detecting device 14 to the inner peripheral surface of the bearing ring 2 but also receives a reflected echo of the ultrasonic pulse, converts the echo into a voltage signal and transmits the voltage signal to the ultrasonic detecting device 14.

The ultrasonic detecting device 14, in accordance with an instruction from the control unit 9, transmits an instruction signal composed of a voltage signal to the ultrasonic detecting probe 3 and also transmits detection information, which is obtained on the basis of its transmitted and received signals, to the control unit 9; and, the control unit 9 displays the detection information on an CRT.

The linear guide device 10 is capable of moving the ultrasonic detecting probe 3 in the axial direction of the bearing ring 2 through a servo motor (not shown) which can be controlled by a linear guide controller 16. The linear guide controller 16, if it is detected that the bearing ring 2 has been rotated once (360°) by a rotary encoder 15 mounted on the outer peripheral surface of the bearing ring 2, controls the servo motor in accordance with an instruction from the control unit 9 to thereby move the ultrasonic detecting probe 3 by a given dimension in the axial direction of the bearing ring 2. As a result, the whole raceway surface of the bearing ring 2 can be detected for presence or absence of a defect.

The detection was carried out according to a water depth detecting method under the following condition.

Detecting probe: Focusing type probe (vibrator diameter of 6 mm)

Frequency: 15 MHz

Also, in this detecting operation, the angle of refraction of an ultrasonic wave entering the bearing ring 2 was set at an angle of 30°, and the angle of refraction of an ultrasonic wave entered was set at an angle of 5°; that is, the detection was carried out in such a manner that the test pieces could be sufficiently detected for the defects thereof up to the 2% Da depth thereof under these incidence conditions.

After the above detecting operation, a life test was conducted on test pieces, that is, cylindrical roller bearings in which the outer races having been found to be free from any defect of 100 microns or more as the result of the above detection are used in combination with the inner races having been found to contain therein large non-metallic inclusions of 500 microns or more and 100 microns or more shown in the test pieces No. 1–No. 5 of Table 1 as the result of the ultrasonic detection.

That is, the bearing life test was conducted under the following conditions using a life tester.

Figure 2:
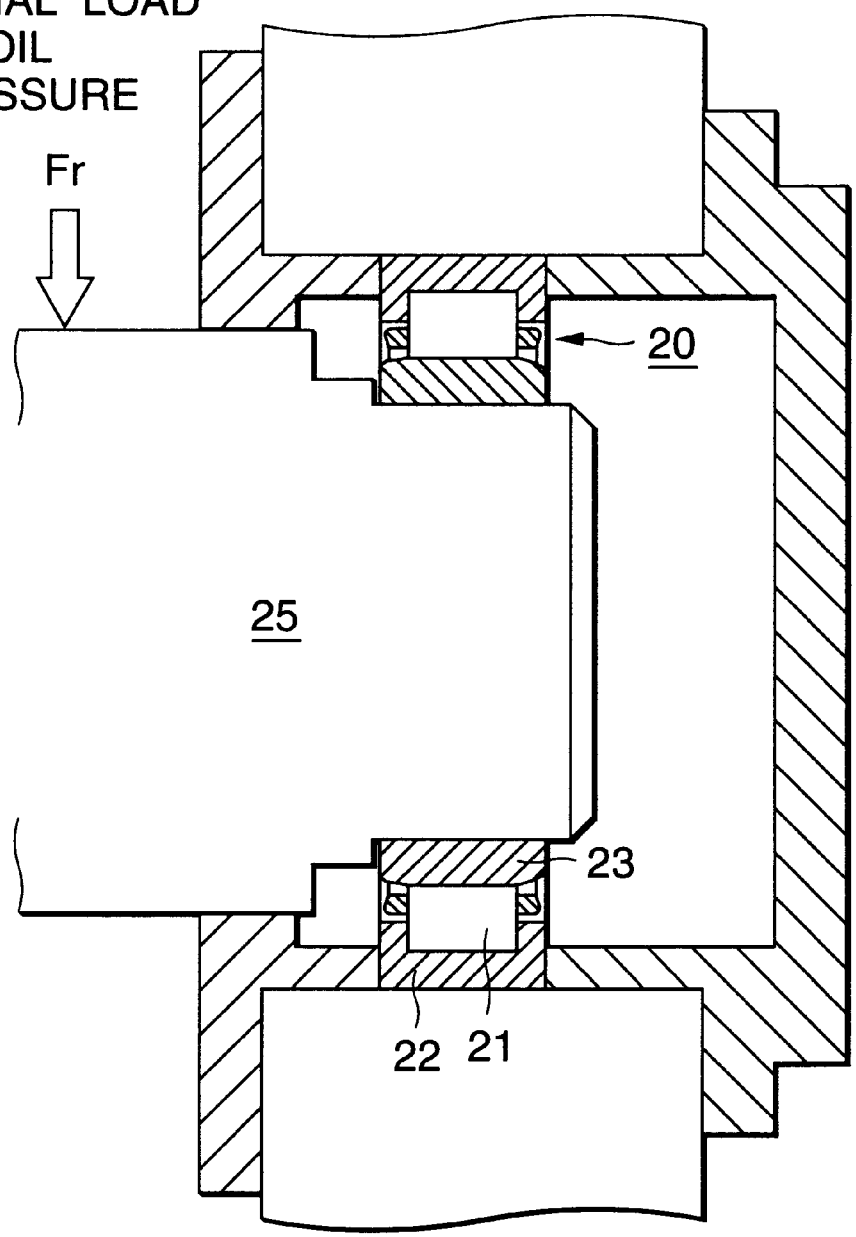

FIG. 2 is a section view of the main portions of the life tester used in the bearing test. An outer triangle race 22 on which a rolling element 21 of a bearing to be tested 20 was incorporated into a housing 24, an inner race 23 was fitted with a rotary shaft (roller) 25, a radial load Fr due to oil pressure was applied to the bearing, and then, while rotating the rotary shaft 25, the life test was conducted.

Bearing: Cylindrical roller bearing NU3336

Radial load: 800 KN (P/C=0.5)

Inner race rotation number: 1000 rpm

Lubrication: Grease

In the embodiments 1 and 2 shown in Table 1, although the steel kinds thereof are respectively SUJ2 and SCR420 and thus are different from each other, in the their respective test piece volumes each consisting of 2% DA depth× raceway surface, not only a non-metallic inclusion of 500 microns or more but also a non-metallic inclusion of 100 microns or more were not found, and no breakaway occurred in the bearings for the bearing life test time exceeding 100 Hrs.

On the other hand, in the comparison example 1, a bearing, the steel kind of which is SCR420, was ultrasonically detected for the defect thereof and found that, on the raceway surface side of the inner race thereof, there were contained two non-metallic inclusions of 500 microns or more and five non-metallic inclusions of 100 microns or more. After then, when a life test was conducted on the present bearing as a test piece, there occurred a breakaway in the bearing in the bearing life test time of 12 Hrs.

In the comparison example 2, a bearing, the steel kind of which is SUJ2, was ultrasonically detected for the defect thereof and found that, on the raceway surface side of the inner race thereof, there were contained a non-metallic inclusion of 500 microns or more and four non-metallic inclusions of 100 microns or more. After then, when a life test was conducted on the present bearing as a test piece, there occurred a breakaway in the bearing in the bearing life test time of 15 Hrs.

In the comparison example 3, a bearing, the steel kind of which is SCR440, was ultrasonically detected for the defect thereof and, on the raceway surface side of the inner race thereof, there was not found any non-metallic inclusion of 500 microns or more but there were found two non-metallic inclusions of 100 microns or more. After then, when a life test was conducted on the present bearing as a test piece, the bearing was found to be improved in life over the above-mentioned comparison examples 1 and 2, but there occurred a breakaway in the bearing in the bearing life test time of 60 Hrs.

From the above test results, to prevent occurrence of a short-life bearing as a finished product, it is effective to restrict the existence of a non-metallic inclusion of 500 microns or more in the range of the 2% Da depth of the raceway surface of a bearing and, especially, to provide the bearing with a long life, it is preferred to restrict the existence of a non-metallic inclusion of 100 microns or more in that range.

Second Embodiment

The present inventors also have checked the impurity components of the steel materials of the bearings which had been found by the ultrasonic detecting method that they contained therein one or more large non-metallic inclusions each having a mean grain diameter of 100 microns or more and further one or more large non-metallic inclusions each having a mean grain diameter of 500 microns or more. As the results of our check, the present inventors have found that, if the contents of oxygen O and sulfur S which are impurity components contained in the steel material are restricted, then the occurrence of the large non-metallic inclusions in the bearing can be reduced.

Specifically, to restrict or reduce the existence of the large non-metallic inclusions of 500 microns or more and further of 100 microns or more to thereby eliminate the occurrence of the short-life product in the bearings, it has been found necessary to reduce the contents of the impurity components, that is, reduce the oxygen content down to 9 ppm or less and the sulfur content down to 0.005% by weight or less.

The reason for the above necessary condition is as follows:

That is, oxygen O exists in steel as inclusion components in the form of oxide-system components such as $Al_2O_3$, CaO, MgO and the like. Also, sulfur S exists as inclusion components in the form of sulfide-system components such as MnS, CaS and the like. It has been also found that, in steel, if these inclusions collect together in a multiple manner, then they exist as non-metallic inclusions each having a given length and a given width, such as $Al_2O_3$—MgO—CaO, $Al_2O_3$—MgO—CaO—MnS and the like.

In other words, if the contents of oxygen and sulfur which are components forming the impurities are respectively controlled down to 9 ppm or less and 0.005% by weight or less, then the occurrence of the non-metallic inclusions each having a mean grain diameter of 500 microns or more and further of 500 microns or more can be controlled, thereby being able to eliminate the occurrence of a short-life bearing as a finished product.

To obtain steel which contains oxygen of 9 ppm or less and sulfur of 0.005% by weight or less as impurity components thereof, it is effective to employ a method in which, after a steel material is resolved in an electric furnace and a blast furnace, the steel material is treated according to a VAR process (a vacuum arm re-resolution process).

Now, description will be given below of a comparison test conducted on embodiments according to the invention and comparison examples.

Similarly to the previously described first embodiment, as test pieces, the components of a NU3336-type cylindrical roller bearing were prepared using steel materials shown in Table 2.

TABLE 2

| Division | No. | Steel Kinds | S(%) | O(ppm) | Number of inclusions 500 μm or more | Number of inclusions 100 μm or more | Bearing Life Test |
|---|---|---|---|---|---|---|---|
| Embodiment 3 | 6 | SUJ2 | 0.003 | 9 | Not found | Not found | 100 Hrs. or longer |
| Embodiment 4 | 7 | SCR420 | 0.005 | 7 | Not found | Not found | 100 Hrs. or longer |
| Embodiment 5 | 8 | SCR440 | 0.005 | 9 | Not found | Not found | 100 Hrs. or longer |
| Comparison example 4 | 9 | SUJ2 | 0.015 | 11 | three | eight | 10 Hrs. |
| Comparison example 5 | 10 | SCR420 | 0.008 | 9 | Not found | two | 83 Hrs. |

Further, as test pieces the impurity components of which are limited, there were prepared bearings, that is, test pieces Nos. 6–10 respectively formed of steel materials containing impurity components (S, O) shown in FIG. 2, by 200s each. And, the raceway surfaces of the inner and outer races of the thus obtained bearings, similarly to the previously described case, were respectively checked by the ultrasonic detecting device to confirm as to whether the given defects (non-metallic inclusions) were present or absent. By the way, similarly to the previously described test pieces Nos. 1–5, for the outer races, there were used steel materials which had been previously confirmed by the ultrasonic detecting device that they did not contain any defect of 500 microns or more or any. defect of 100 microns or more, only the inner races were checked for the size and number of the non-metallic inclusions thereof.

Referring here to a checking or evaluating method employed in the above comparison test, all the test pieces of the respective inner races (that is, 200 each test piece) were detected ultrasonically under the same condition as in the first embodiment, and were checked for the number of bearings in which the non-metallic inclusions of 500 microns or more were found present in the test piece volume range of 2% Da depth×raceway surface. Also, there were confirmed the number of bearings in which the non-metallic inclusions of 100 microns or more were found present.

Next, in the case of the bearings in which the non-metallic inclusions were found present, as a representative of them, the bearing containing the largest inclusion was selected; and, in the case of the bearings with no inclusion found, one of them was selected at random. A life test was conducted on the two selected bearings.

In the embodiments 3, 4 and 5 shown in Table 2, because the steel kinds thereof were respectively SUJ2, SCR420 and SCR440 and also because there were used steel materials the impurity components S and O of which were respectively within the limit range (S: 0.05% or less, O: 9 ppm or less) specified by the invention, there was found no non-metallic inclusion of 500 microns or more in the test piece volume of 2% Da depth×raceway surface of each bearing as the finished product. Also, a life test was conducted on the representative bearings of the respective embodiments similarly to the first embodiment. As the results of the life test, it was confirmed that, even for a life test time of 100 Hrs. or longer, no breakaway occurred in the bearings.

On the other hand, in the comparison example 4 in which the impurity components S and O of the steel material thereof exceeded the above-mentioned limit range, out of the bearings as the finished products thereof, there were detected three bearings each containing one or more non-metallic inclusions of 500 microns or more in the test piece volume of 2% Da depth×raceway surface of inner race thereof, and 8 bearings each containing one or more non-metallic inclusions of 100 microns or more in the same test piece volume. Among the bearings found containing one or more non-metallic inclusions of 500 microns or more, the bearing containing the largest non-metallic inclusion was subjected to a life test. This life test showed that the bearing broke away in a life test time of 10 Hrs., that is, the life of the bearing was very short.

Next, in the comparison example 5 in which sulfur S of the impurity components of the steel material thereof exceeded the above limit range, there was found no bearing containing one or more non-metallic inclusions of 500 microns or more in the test piece volume of 2% Da depth× raceway surface of inner race thereof, but there were found 2 bearings each containing one or more non-metallic inclusions of 100 microns or more in the same test piece volume. Out of the two bearings found containing one or more non-metallic inclusions of 100 microns or more, the bearing containing the largest non-metallic inclusion was subjected to a life test. This life test showed that the bearing broke away in a life test time of 83 Hrs., that is, the life of the bearing was longer than that of the comparison example 4 but was much shorter than the embodiments of the invention.

From the foregoing test results, it can be clearly understood that use of a steel material containing, as impurity components thereof, S of 0.05% or less and O of 9 ppm or less is able to restrict the existence of large non-metallic inclusions each of 500 microns or more and 100 microns or more in a bearing as a finished product, and thus can eliminate the occurrence of a short-life bearing.

As has been described heretofore, according to the present invention, there is employed, as a test piece volume range, a range expressed by the product of a 2% Da depth, where a shearing stress to be generated when the inner or outer race of a bearing and a rolling element are rollingly contacted with each other provides the largest value, and the raceway surface of the inner or outer race of the bearing; and, using the test piece volume range, the size and existence of non-metallic inclusions are restricted over all the bearings as finished products. Thanks to this, differently from the conventional purity restriction based on sample evaluations, the present invention can provide an excellent effect that, even under a severe using condition of a high load and a high surface pressure, unexpected occurrence of a short-life bearing can be prevented and thus the stable life of a bearing can be guaranteed.

What is claimed is:

1. A rolling bearing comprising:

at least one of an inner race and an outer race;

a plurality of rolling elements rollingly movable on the inner or outer race, wherein no non-metallic inclusion has a length of more than 500 $\mu$m within a volume of 2% Da multiplying raceway surface area of at least one of said inner and outer race, where said 2% Da depth expresses a depth which ranges from the surfaces of the inner and outer races and rolling elements of the bearing to 2% of the mean diameter of the rolling elements.

2. A rolling bearing as set for the in claim 1, wherein no non-metallic inclusion has a length more than 100 $\mu$m.

3. A rolling bearing as set forth in claim 2, wherein impurity components within said test piece volume defined by multiplying 2% Da by raceway surface of at least one of said inner are outer race includes Oxygen 9 ppm or less and Sulfur 50 ppm or less.

4. A rolling bearing as set forth in claim 1, wherein impurity components within said volume defined by multiplying 2% Da by raceway surface area of at least one of said inner are outer race includes Oxygen 9 ppm or less and Sulfur 50 ppm or less.

* * * * *